(12) United States Patent
Srivastava et al.

(10) Patent No.: US 12,109,373 B2
(45) Date of Patent: Oct. 8, 2024

(54) DEVICES AND SYSTEMS FOR AN ENDOSCOPIC PROCEDURE

(71) Applicant: Boston Scientific Scimed, Inc., Maple Grove, MN (US)

(72) Inventors: Kyle H. Srivastava, Saint Paul, MN (US); Vijay Koya, Blaine, MN (US); Jonathan B. Shute, Eagan, MN (US); Christopher Piere, Hudson, WI (US); Mark Kringle, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 215 days.

(21) Appl. No.: 17/473,483

(22) Filed: Sep. 13, 2021

(65) Prior Publication Data
US 2022/0080154 A1 Mar. 17, 2022

Related U.S. Application Data

(60) Provisional application No. 63/078,544, filed on Sep. 15, 2020.

(51) Int. Cl.
*A61M 25/01* (2006.01)
*A61M 25/00* (2006.01)

(52) U.S. Cl.
CPC . *A61M 25/0136* (2013.01); *A61M 2025/0002* (2013.01); *A61M 2205/0294* (2013.01);
(Continued)

(58) Field of Classification Search
CPC ......... A61B 18/1492; A61B 2090/065; A61M 2025/0002
See application file for complete search history.

(56) References Cited

U.S. PATENT DOCUMENTS

| 4,757,194 A | 7/1988 | Simms |
| 5,024,617 A | 6/1991 | Karpiel |

(Continued)

FOREIGN PATENT DOCUMENTS

| EP | 3298978 A1 | 3/2018 |
| JP | 54-89893 U | 1/1979 |

(Continued)

OTHER PUBLICATIONS

WO2020158572 machine translation (Year: 2020).*

(Continued)

*Primary Examiner* — Laura A Bouchelle
(74) *Attorney, Agent, or Firm* — Seager, Tufte & Wickhem, LLP

(57) ABSTRACT

A navigation-assisting flexible elongate member, a navigation-assisting system, and a navigation-assisting method for use in navigating within a body to a treatment site. A navigation-assisting sensor, such as an optic fiber, an inductive sensor, a piezoelectric sensor, or a camera, is provided within the wall of the flexible elongate member, so as not to occupy space within a working channel defined by and through the flexible elongate member. When the distal end of the flexible elongate encounters an obstacle/another object (e.g., body tissue or a lumen wall), the navigation-assisting sensor generates a signal indicative of such encounter. Such signal is converted into information (such as by a control unit) usable to navigate the flexible elongate member away from the obstacle and on course to the treatment site.

20 Claims, 5 Drawing Sheets

(52) U.S. Cl.
    CPC .............. *A61M 2205/3317* (2013.01); *A61M 2205/3331* (2013.01)

(56) References Cited

U.S. PATENT DOCUMENTS

| | | | |
|---|---|---|---|
| 5,547,469 | A | 8/1996 | Rowland et al. |
| 5,868,698 | A | 2/1999 | Rowland et al. |
| 5,951,495 | A | 9/1999 | Berg et al. |
| 6,027,499 | A * | 2/2000 | Johnston ............... A61B 34/35 606/22 |
| 6,235,026 | B1 | 5/2001 | Smith |
| 6,676,659 | B2 | 1/2004 | Hutchins et al. |
| 6,827,718 | B2 | 12/2004 | Hutchins et al. |
| 7,371,237 | B2 | 5/2008 | Hutchins et al. |
| 7,635,363 | B2 | 12/2009 | Hutchins et al. |
| 7,689,071 | B2 | 3/2010 | Belleville et al. |
| 8,048,063 | B2 * | 11/2011 | Aeby ............ A61B 17/320758 606/1 |
| 8,066,703 | B2 | 11/2011 | Adams |
| 8,192,368 | B2 | 6/2012 | Woodruff et al. |
| 8,231,621 | B2 | 7/2012 | Hutchins et al. |
| 8,579,895 | B2 | 11/2013 | Hutchins et al. |
| 9,913,570 | B2 * | 3/2018 | Kucharski ............... A61B 1/018 |
| 10,238,295 | B2 | 3/2019 | Hellstrom et al. |
| 10,258,240 | B1 | 4/2019 | Eberle et al. |
| 10,537,255 | B2 | 1/2020 | Eberle et al. |
| 10,582,860 | B2 | 3/2020 | Gregorich et al. |
| 2001/0034501 | A1 | 10/2001 | Tom |
| 2005/0062979 | A1 | 3/2005 | Zhu et al. |
| 2008/0275428 | A1 | 11/2008 | Tegg et al. |
| 2009/0138007 | A1 | 5/2009 | Govari et al. |
| 2009/0306650 | A1 | 12/2009 | Govari et al. |
| 2011/0004198 | A1 | 1/2011 | Hoch |
| 2017/0172509 | A1 | 6/2017 | Hein et al. |
| 2018/0338811 | A1 | 11/2018 | Miklos et al. |
| 2019/0254649 | A1 | 8/2019 | Walters et al. |

FOREIGN PATENT DOCUMENTS

| | | | | |
|---|---|---|---|---|
| JP | 2007202927 | A | | 8/2007 |
| JP | 4994244 | B2 | | 8/2012 |
| WO | 2009085108 | A1 | | 7/2009 |
| WO | 2015069887 | A | | 5/2015 |
| WO | 2018047796 | A1 | | 3/2018 |
| WO | WO-2020158572 | A1 | * | 8/2020 ......... A61B 5/02154 |

OTHER PUBLICATIONS

"SpyGlass DS II Direct Visualization System" Boston Scientific—Mar. 2019, 10 pages.
"RX Biliary System" Boston Scientific—Feb. 2016, 19 pages.
Kethu et al., "ERCP cannulation and sphincterotomy devices" Gastrointest Endosc. Mar. 2010;71(3):435-45. doi: 10.1016/j.gie.2009.07.038.
"Biliary Access" Boston Scientific—13 pages.
"Sphincterotome—an overview" ScienceDirect—retrieved Mar. 13, 2020, 23 pages (including texts dated 2008 and 2011).
"INTELLANAV™ Open-Irrigated Ablation Catheter" Boston Scientific—retrieved Mar. 6, 2020, 3 pages.
Koksal et al., "Biliary endoscopic sphincterotomy: Techniques and complications" World J Clin Cases Dec. 26, 2018; 6(16): 1073-1086.
Edmundowicz, Steven. "Wire Guided Cannulation: Clinical Perspective—A Review of the Literature and Appraisal of the Technique" Boston Scientific—Mar. 2013, 4 pages.
Author Unknown, "Pressure Sensors: The Design Engineer's Guide: Optical pressure sensors" Avnet Abacus—retrieved Mar. 20, 2020 URL: https://www.avnet.com/wps/portal/abacus/solutions/technologies/sensors/pressure-sensors/core-technologies/optical/.
International Search Report and Written Opinion for the International Patent Application No. PCT/US2021/050075, mailed Jan. 4, 2022, 14 pages.

* cited by examiner

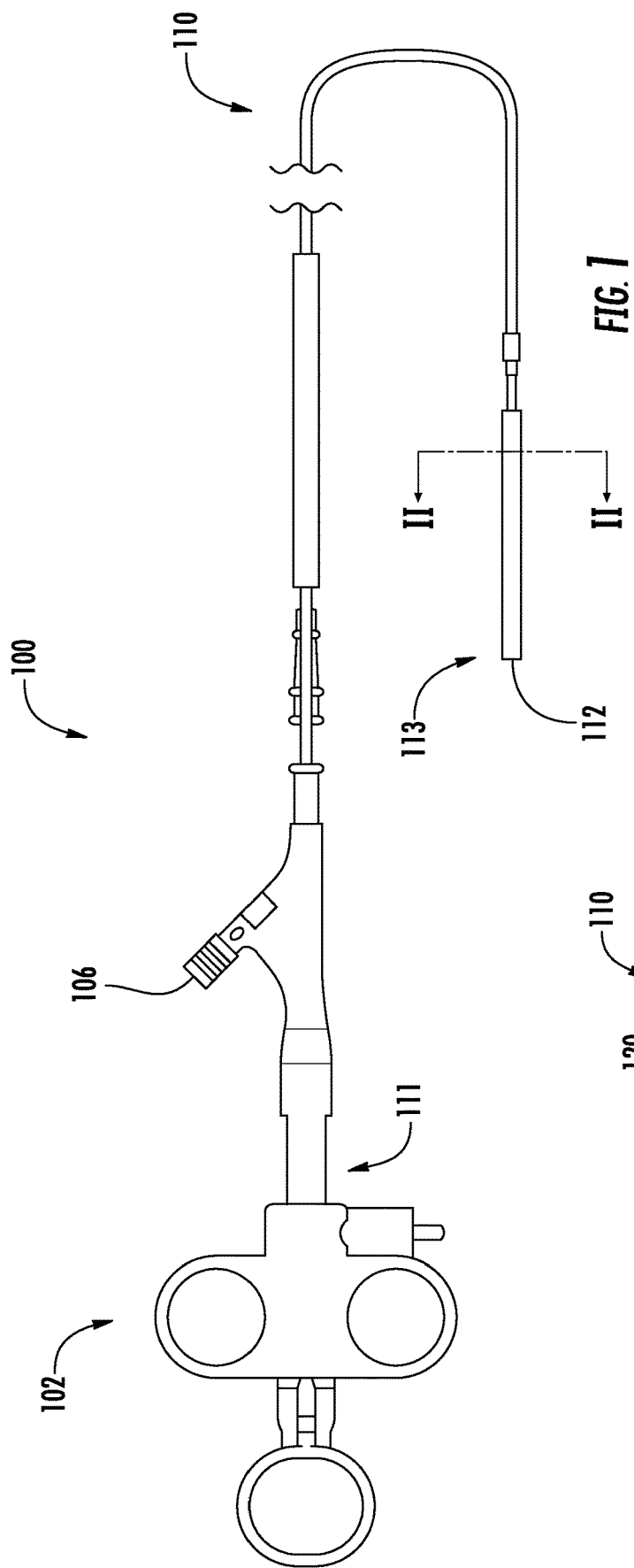
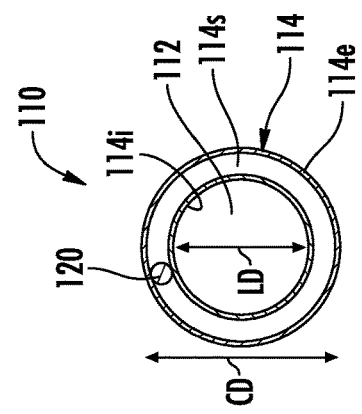
FIG. 1
FIG. 2

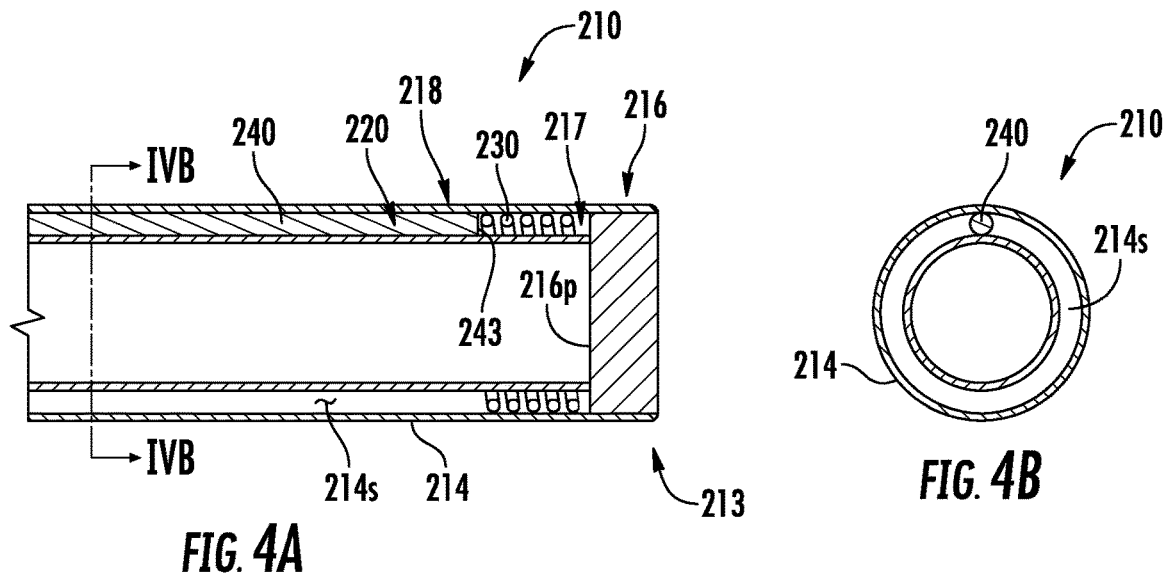
FIG. 4A
FIG. 4B
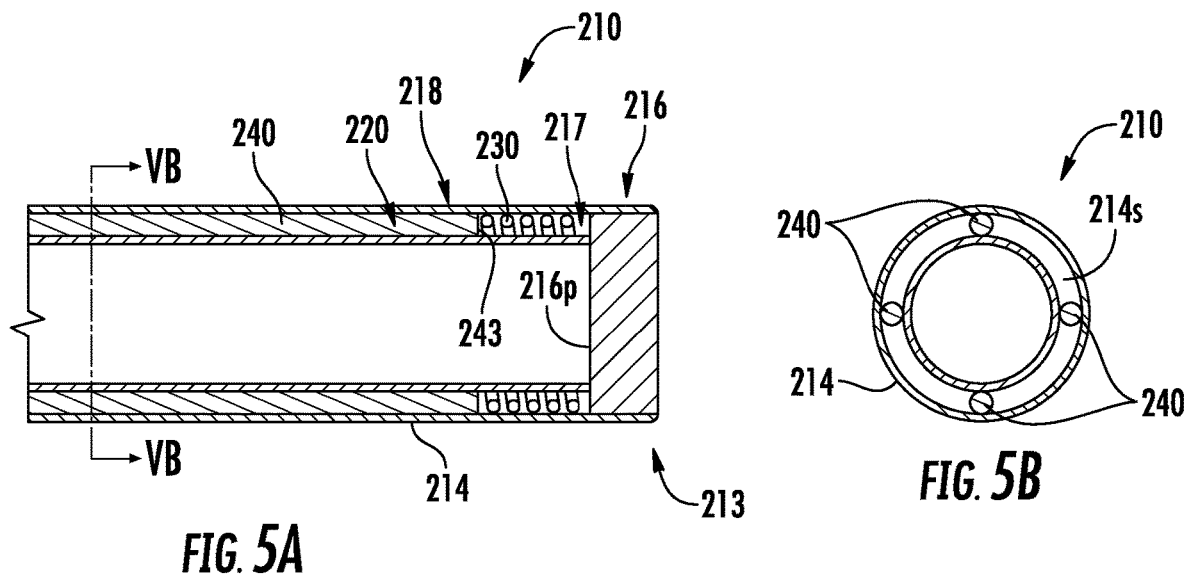
FIG. 5A
FIG. 5B

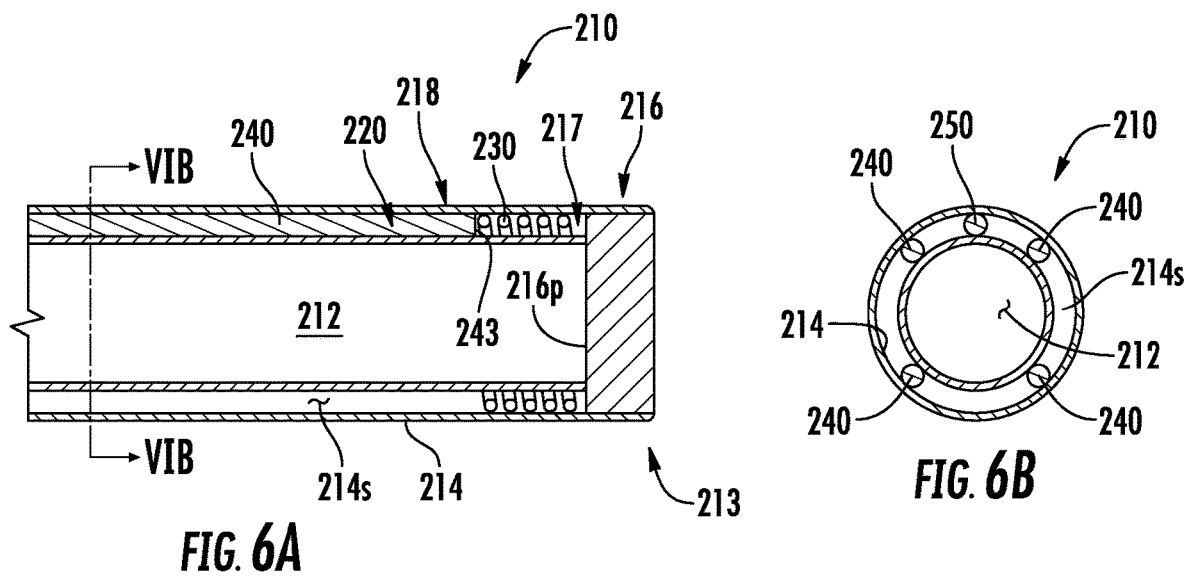
FIG. 6A
FIG. 6B
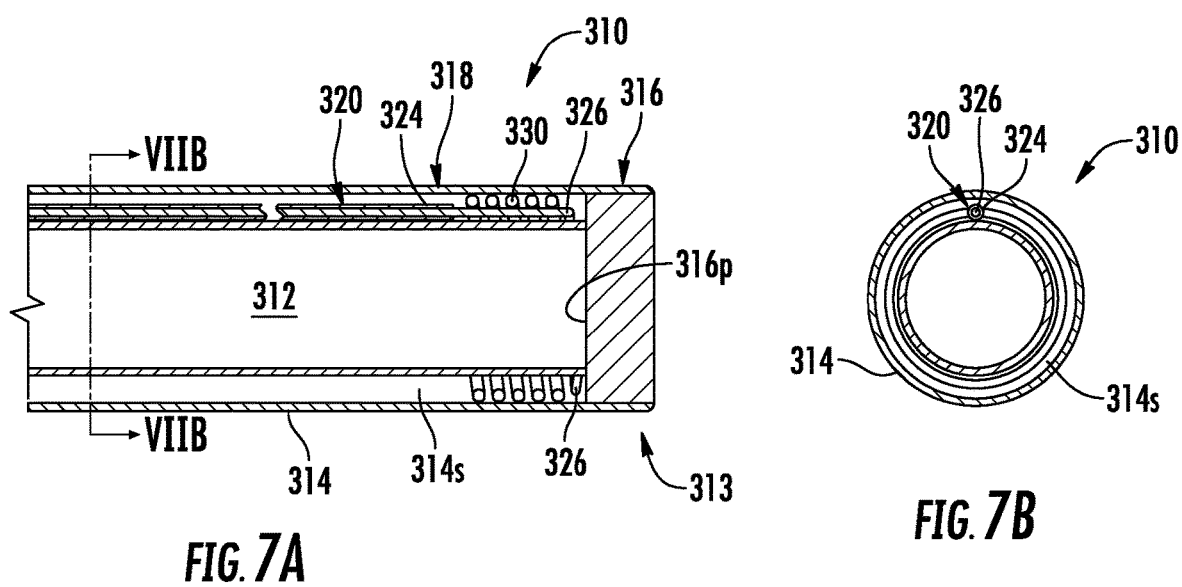
FIG. 7A
FIG. 7B

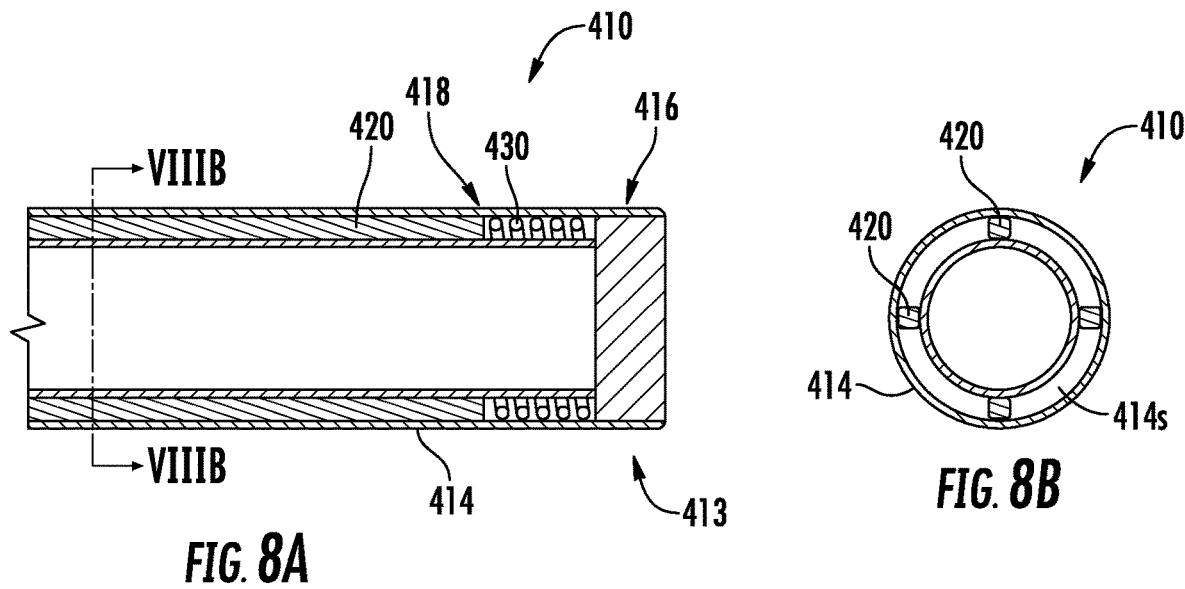
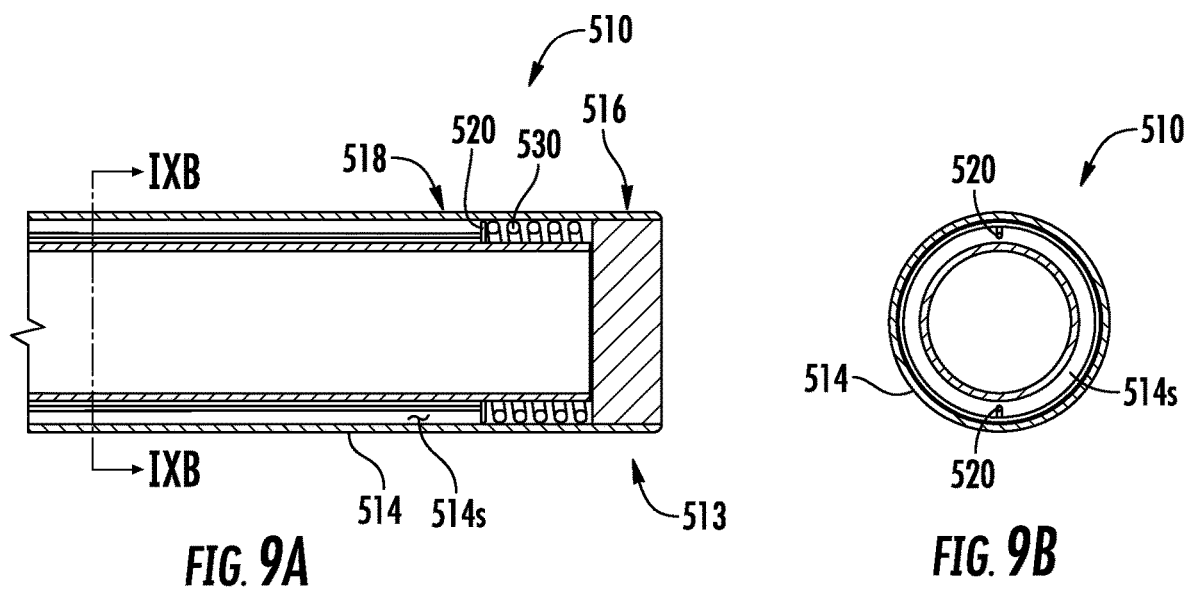

DEVICES AND SYSTEMS FOR AN ENDOSCOPIC PROCEDURE

PRIORITY

The present application is a non-provisional of, and claims the benefit of priority under 35 U.S.C. § 119 to, U.S. Provisional Application Ser. No. 63/078,544, filed Sep. 15, 2020, the disclosure of which is hereby incorporated herein by reference in its entirety for all purposes.

FIELD

The present disclosure relates generally to the field of catheters. In particular, the present disclosure relates to catheters with navigation-assisting capabilities, such as with navigation-assisting components or equipment, such as for use within a body.

BACKGROUND

In various procedures, such as gastrointestinal procedures, such as cannulations, physicians or other medical professionals must navigate complex anatomy with a limited amount of feedback (visual, tactile, etc.). For example, a target body passageway may be oriented at a difficult angle relative to an endoscopic accessory tool, have a very small or sealed opening, or include a tortuous anatomy, blockages, and/or benign or malignant structures. Medical professionals may make multiple attempts to achieve successful cannulations. Further, the likelihood of causing trauma to the tissues comprising or surrounding the target body passageway increases with the number of cannulation attempts.

Accordingly, there is a need in the art for ways to improve the success of cannulation procedures.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a flexible elongate member, such as of a navigation-assisting catheter and system, is provided with various components capable of determining position of the catheter relative to another object (e.g., tissue wall or lumen wall) and conveying such information for use in navigating, directing, maneuvering, etc., the catheter. In some embodiments, the flexible elongate member includes a navigation-assisting sensor generating signals which are usable or translatable into information usable in navigating the flexible elongate member, such as within a body cavity or lumen. Such flexible elongate member and associated system are useful in navigating with respect to a bile duct, a pancreatic duct, or any lumen, potentially for use in any of a variety of gastrointestinal, urinary, reproductive, cardiovascular, respiratory, pulmonary, etc., procedures. While the present disclosure may refer to navigation with respect to the gastrointestinal system and/or biliary ducts as examples, the disclosed devices, systems, and methods should not be understood as being limited to such examples.

In various embodiments described or otherwise within the scope of the present disclosure a flexible elongate member is disclosed as including an exterior wall and interior wall defining an interior space therebetween and a working channel therein, and extending axially between a proximal end of the flexible elongate member and a distal end of the flexible elongate member; and at least one sensor, such as a pressure sensor, positioned within the interior space; where at least one of the exterior wall and the interior wall defines a flexible distal end of the flexible elongate member; and the at least one sensor is positioned in the distal end of the flexible elongate member.

In some embodiments, the at least one sensor includes at least three pressure sensors providing directional information. In some embodiments, the at least one pressure sensor includes at least four pressure sensors equidistantly spaced about the periphery of the interior space.

In some embodiments, the at least one sensor detects impact of the distal end of the flexible elongate member against an object.

In some embodiments, the at least one sensor includes one of an optic fiber, an inductive sensor, or a piezoelectric sensor.

In some embodiments, the distal end of the flexible elongate member includes a proximal pressure sensing segment and a distal pressure sensing segment axially movable with respect to each other.

In some embodiments, the flexible elongate member further includes a biasing element biasing the proximal pressure sensing segment and the distal pressure sensing segment apart in a neutral configuration when the distal end of the flexible elongate member is not impacting and object.

In some embodiments, at least one pressure sensor is provided in the proximal pressure sensing segment, and movement of the distal pressure sensing segment relative to the proximal pressure sensing segment actuates the at least one pressure sensor to generate a signal. In some embodiments, the signal is indicative of the distal end of the flexible elongate member impacting an object.

In some embodiments, the at least one sensor includes at least three pressure sensors spaced apart to indicate directionality of impact to the distal end of the flexible elongate member.

In some embodiments, the at least one sensor is a fiber optic with a distal end at a distal end of the proximal pressure sensing segment spaced apart from a proximal face of the distal pressure sensing segment, and movement of the distal pressure sensing segment relative to the proximal pressure sensing segment causes a change in the interference pattern generated by reflection of light from the fiber optic against the proximal face of the distal pressure sensing segment indicative of pressure on the distal end of the flexible elongate member.

In some embodiments, the flexible elongate member further includes a camera within the interior space.

In various embodiments described or otherwise within the scope of the present disclosure a flexible elongate member is disclosed as including an exterior wall and interior wall defining an interior space therebetween and a working channel therein, and extending axially between a proximal end of the flexible elongate member and a distal end of the flexible elongate member; and at least one navigation-assisting sensor positioned within the interior space in a distal end of the flexible elongate member to generate a signal indicative of the distal end of the flexible elongate member encountering an object.

In some embodiments, the at least one navigation-assisting sensor is a pressure sensor capable of detecting impact of the distal end of the flexible elongate member against an object. In some embodiments, the at least one pressure sensor includes at least three pressure sensors providing directional information. In some embodiments, the at least one pressure sensor includes at least four pressure sensors equidistantly spaced about the periphery of the interior space.

In some embodiments, the at least one navigation-assisting sensor includes one of an optic fiber, an inductive sensor, a piezoelectric sensor, or a camera. Other sensors, such as proximity, light, temperature, etc. are within the scope of the present disclosure as well.

In one aspect, the present subject matter is directed to a navigation-assisting system including a handle housing navigational equipment; a flexible elongate member extending axially between a proximal end coupled to the handle and a distal end, and including an exterior wall and interior wall defining an interior space therebetween and a working channel therein; and at least one navigation-assisting sensor positioned within the interior space in the distal end of the flexible elongate member to generate a signal indicative of the distal end of the flexible elongate member encountering an object; wherein at least one of the exterior wall and the interior wall defines a distal end of the flexible elongate member, and the at least one navigation-assisting sensor is positioned in the distal end of the flexible elongate member.

In some embodiments, the at least one navigation-assisting sensor includes one of an optic fiber, an inductive sensor, a piezoelectric sensor, or a camera. Other sensors, such as proximity, light, temperature, etc. are within the scope of the present disclosure as well.

In some embodiments, the navigation-assisting system further includes a control unit processing signals from the at least one navigation-assisting sensor to indicate directional information with regard to impact of the distal end of the flexible elongate member against an object.

These and other features and advantages of the present disclosure will be readily apparent from the following detailed description, the scope of the claimed invention being set out in the appended claims.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 1 is an elevational view of a system for navigating complex anatomy in accordance with aspects of the present disclosure.

FIG. 2 is a cross-sectional view along line II-II of the system of FIG. 1.

FIG. 4A is a cross-sectional view along the longitudinal axis of an example of an embodiment of a distal end of a catheter which may be used in the system of FIG. 1.

FIG. 4B is a cross-sectional view along line IV-IV of the embodiment of FIG. 4A.

FIG. 5A is a cross-sectional view along the longitudinal axis of an example of an embodiment of a distal end of a catheter which may be used in the system of FIG. 1.

FIG. 5B is a cross-sectional view along line V-V of the embodiment of FIG. 5A.

FIG. 6A is a cross-sectional view along the longitudinal axis of an example of an embodiment of a distal end of a catheter which may be used in the system of FIG. 1.

FIG. 6B is a cross-sectional view along line VI-VI of the embodiment of FIG. 6A.

FIG. 7A is a cross-sectional view along the longitudinal axis of an example of an embodiment of a distal end of a catheter which may be used in the system of FIG. 1.

FIG. 7B is a cross-sectional view along line VII-VII of the embodiment of FIG. 7A.

FIG. 8A is a cross-sectional view along the longitudinal axis of an example of an embodiment of a distal end of a catheter which may be used in the system of FIG. 1.

FIG. 8B is cross-sectional view along line VIII-VIII of the embodiment of FIG. 8A.

FIG. 9A is a cross-sectional view along the longitudinal axis of an example of an embodiment of a distal end of a catheter which may be used in the system of FIG. 1.

FIG. 9B is cross-sectional view along line IX-IX of the embodiment of FIG. 9A.

DETAILED DESCRIPTION

Figure 3:
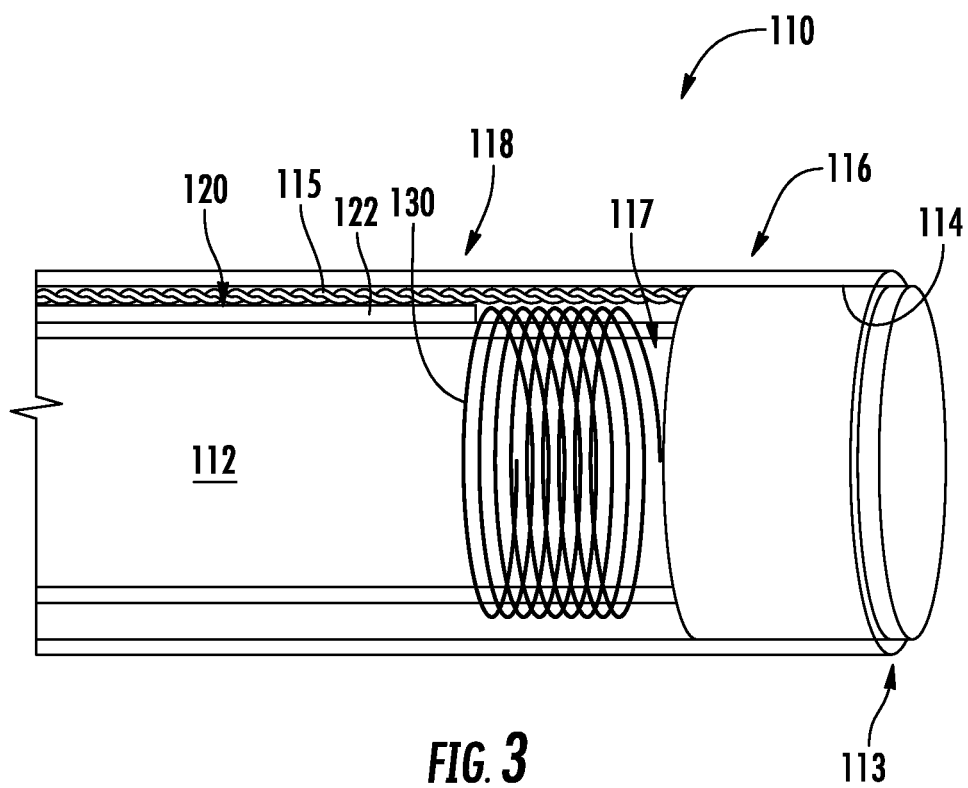
FIG. 3 is an enlarged isolated perspective view of the distal end of the catheter of the system of FIG. 1 with navigation-assisting components illustrated schematically.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, or a bore.

Various treatment devices, equipment, etc. may be delivered via a delivery device which generally includes a flexible elongate member with one or more working channels extending substantially longitudinally (axially) between the proximal end and the distal end of the delivery device. It is generally beneficial for the delivery device to be steerable, and the delivery device may have different areas of different flexibility or stiffness to promote steerability. The delivery devices and/or overtubes associated therewith may be made from any suitable biocompatible material known to one of ordinary skill in the art and having sufficient flexibility to traverse non-straight or tortuous anatomy. Such materials include, but are not limited to, rubber, silicon, synthetic plastic, stainless steel, metal-polymer composite; metal alloys of nickel, titanium, copper cobalt, vanadium, chromium, and iron; superelastic or shape memory material such as nitinol (nickel-titanium alloy); different layers of different materials and reinforcements. Such materials may be made of or coated with a polymeric or lubricious material to enable or facilitate passage of a deliver device therethrough. In some embodiments, the working channels may be made of or coated with a polymeric or lubricious material to facilitate passage of the introduced medical instrument(s) through the working channel(s).

It is generally recognized that it is difficult to accurately and consistently position a device, such as a sphincterotome or papillotome, for proper cannulation. Steering through a tortuous body lumen, such as the tortuous pathway within the intestines, requires multiple turns of the delivery device. As may be appreciated, the medical professional may inadvertently advance the tip of the delivery device or flexible elongate member or catheter or cannula or other device or equipment (such terms used interchangeably herein without limitation, "catheter" generally being used for the sake of simplicity without intent to limit) against a wall of the lumen rather than continuing to advance through the lumen. Such advancement may irritate the tissue, or even puncture the wall, and may lead to further complications. Similarly, because of variations in anatomy from patient to patient, there is not always a clear access path to the biliary duct or the pancreatic duct via the papilla, or e.g., in pulmonary navigation. A cannula may be inserted as a result of trial and error advances against the papilla in an attempt to locate access therethrough.

In accordance with one aspect of the present disclosure, in a cannulation procedure in which proper and careful guidance of the cannula or catheter or scope (or other component, such terms being used interchangeably herein without intent to limit) is desired to reach the treatment site without impacting tissue en route thereto, it is desirable to achieve minimal to no pressure against the distal end of the catheter. In accordance with the present disclosure, a navigation-assisting sensor is provided in the distal tip of the delivery device or flexible elongate member or catheter (or other component with a lumen therethrough, such terms being used interchangeably herein without intent to limit) to provide feedback to the medical professional so that the medical professional is aware if the catheter tip encounters a lumen wall and may halt advancement of the catheter to avoid injuring or puncturing the tissue and/or lumen wall. Any type of sensor, such as a pressure, proximity, light, temperature, etc. sensor, known or heretofore known to those of ordinary skill in the art suitable for use in a body passage, and/or of suitable size and dimension, and/or capable of high sensitivity sensing may be used. For instance, fiber optic, inductive, or piezoelectric sensors may be used. In some embodiments, the sensor is configured to provide directional information to the medical professional to assist in steering the catheter through the lumen. Such directional information may be useful in avoiding contact of the catheter tip with the lumen wall as well as assisting with navigation in a more general manner. A navigation-assisting (e.g., pressure-sensing) device as described herein may be any suitable for use with any cannulation device or catheter or other structure (used interchangeably herein without intent to limit) of any size, cross-sectional shape or area, and/or configuration permitting introduction and passage into a body or part of the anatomy, such as in or through a body lumen or duct. Navigation-assisting equipment and components as described herein are particularly suited for arrangement within a wall of a flexible elongate member such as a tubular structure such as a catheter. The flexible elongate member generally includes a working channel (preferably extending axially along the length or longitudinal axis of the catheter) to facilitate navigation to treatment site by advancing the elongate member over a guidewire (extending through the working channel). The working channel may also permit delivery of various therapies or other treatment equipment therethrough. The navigation-assisting equipment is housed within (e.g., between the walls of) the catheter and thus may be protected from debris accessing and interfering with operation of the sensor.

As may be appreciated, the navigation-assisting equipment or components (or at least a portion thereof) preferably are positioned at the distal end of the flexible elongate member. As such, engagement of the distal end of the flexible elongate member with another object will be sensed by the navigation-assisting equipment and information generated and conveyed to the user (medical professional, etc., or other navigator of the medical equipment) for use in further navigational decisions. Preferably, the distal end of the flexible elongate member is sufficiently flexible to transfer impact thereto to the navigation-assisting equipment to generate the appropriate information for assisting with navigation of the flexible elongate member and associated equipment and devices. In some embodiments, the distal end of the catheter has a proximal segment and a distal segment with a biasing element (e.g., a coil spring) therebetween. As the distal segment moves or deflects or otherwise deforms (such as upon contact with an object encountered by the distal end of the flexible elongate member), the distal segment translates proximally toward the proximal segment to actuate the navigation-assisting equipment or components thereof. In some embodiments, the biasing element functions to channel forces to the navigation-assisting equipment, such as sensing components thereof, and, in doing so, essentially translates and/or amplifies the forces to facilitate or enhance sensing thereof. Feedback from the navigation-assisting equipment may be directional, such as indicative of whether the dorsal, ventral, left, or right side of the flexible elongate member has been impacted, so that flexible elongate member can be manipulated as appropriate (such as to relieve pressure on the distal end thereof). The navigation-assisting equipment may include at least three pressure sensors to generate information including force magnitude, force attitude (axial or radial force application), and force direction along the periphery of the catheter (e.g., location of load applied along the external periphery of the catheter), or four or more sensors to isolate sensors from other elements and to indicate a quadrant of the distal end of the flexible elongate member which has encountered another object so that the flexible elongate member can be steered to relieve the pressure on the distal end thereof.

Turning now to the drawings, it will be appreciated that in the following description, elements or components similar among the various illustrated embodiments are generally designated with the same reference numbers increased by 100 and redundant description is omitted. Common features are identified by common reference elements and, for the sake of brevity, the descriptions of the common features are generally not repeated.

In various embodiments described herein, a catheterization system 100, such as illustrated in FIG. 1, is provided with a flexible elongate member such as a catheter 110 (as noted above, the term "catheter" being used for the sake of simplicity and without intent to limit) having a working channel 112 extending therethrough along the length thereof (alternately referenced herein as extending axially) between a proximal end 111 of the catheter 110 and a distal end 113 of the catheter 110. The catheter 110 is formed of a sufficiently flexible material to allow flexing of the catheter 110 through tortuous pathways. In some embodiments, the catheter 110 is formed of polytetrafluoroethylene (PTFE), fluorinated ethylene propylene (FEP), polyether ether ketone (PEEK), or the like, or a combination thereof. In some embodiments, the catheter 110 is machined to have greater flexibility in certain regions along the axial extent thereof. It will be appreciated that although reference is made specifically to a catheter, any flexible elongate member capable of housing navigation-assisting equipment as described herein may be used.

A proximal end 111 of the catheter 110 extends to a control handle 102 via which the medical professional may manipulate and/or control and/or navigate and/or steer (such terms being used interchangeably herein for the sake of convenience, use of one term over another not to be understood as limiting) the catheter 110 (or an endoscope or duodenoscope or bronchoscope or other apparatus via which the catheter 110 is carried to a treatment site). It will be appreciated that any known or heretofore known control handle 102, such as formed of metallic or polymeric materials, and including one or more connectors (e.g., for coupling other components or devices or equipment thereto), ports (e.g., for injection of fluids such as contrast fluids, such as for fluoroscopy), or other structures or componentry, and capable of housing navigation-assisting equipment as described herein may be used, the catheter 110 of the present disclosure not being limited by a particular handle or configuration thereof. As is generally appreciated, a medical professional may use the control handle 102, or other appropriate guidance equipment known or heretofore known in the art, to rotate, oscillate, linearly advance, reciprocate, and/or otherwise move/guide/navigate the catheter 110 (such as through a body lumen), and, more particularly, to guide the distal end 113 of the catheter 110, to a treatment site, such as to perform a procedure utilizing a catheter (e.g., optionally with a camera, baskets, cutting devices, lasers, or other additional devices), such as endoscopic cannulation procedures, papillotomies, sphincterotomies, uro-procedures, etc.

In accordance with various principles of the present disclosure, the catheter 110 is formed such that navigation-assisting equipment extends (in a generally axial or longitudinal direction) along the wall 114 of the catheter 110. As used herein, navigation-assisting equipment is to be understood as equipment or components or devices providing information, such as positional information, to the user or technician to be used in determining navigation (e.g., navigation decisions), including direction of navigation, of the catheter 110. Examples include, without limitation, pressure sensors and/or cameras, as will be described in further detail below. In accordance with one aspect of the present disclosure, the wall 114 of the catheter 110 has an interior space 114s therein so that the navigation-assisting equipment may be positioned within the wall 114 of the catheter 110. The position of the navigation-assisting equipment within a wall of the catheter 110 leaves the working channel 112 clear for passage of a guidewire, cables, medical instruments, cutting instruments, other working tools, etc. through the working channel 112 within the catheter 110 without interference with the components of the navigation-assisting equipment.

As illustrated in the schematic cross-sectional view of FIG. 2 (along line II-II of FIG. 1), in one embodiment the catheter wall 114 includes an interior wall 114i and an exterior wall 114e defining the interior space 114s therebetween. In one embodiment, the interior wall 114i is an inner liner, and the catheter 110 is a braided catheter having a braided element 115, such as formed over the inner liner (or an inner liner may be provided within the braided catheter, such as to form a lining for the working channel 112, after formation of the braided catheter), and covered, such as by extrusion, with the exterior wall 114e, such as in the form of an outer jacket or layer covering the braided catheter, as known in the art, such as described in U.S. Pat. No. 5,951,495 to Berg (assigned to Boston Scientific Scimed Inc.), titled Catheter Having An Adhesive Braid Wire Constraint And Method Of Manufacture, which patent issued on Sep. 14, 1999, and is incorporated by reference herein in its entirety for all purposes. Such braiding may be beneficial in building up the structure of the catheter while still permitting the desired amount of flexibility for navigational purposes. The navigation-assisting equipment may be mounted between the inner liner and the braided catheter (and, optionally mounted on the inner liner before formation or placement of the braided catheter over the inner liner, or mounted to the braided catheter), in an interior space 114s of the catheter wall 114. In another embodiment, the catheter 110 is formed, such as by extrusion, to have a hollow wall (double wall with space between the double walls) defining a working channel 112 therein. The navigation-assisting equipment may be mounted within the interior space 114s defined between the interior wall 114i and the exterior wall 114e of the hollow wall 114 of such catheter. The distal end 113 of the catheter 110 may be compressible, with a membrane or the exterior wall 114e sealing and protecting the components therein. For the sake of simplicity and convenience, and without intent to limit, embodiments of catheters illustrated in the drawings do not all illustrate a braided catheter.

As may be appreciated, the working channel 112 may be in the form of a lumen sized and configured, e.g., having a lumen diameter LD (as illustrated by FIG. 2, showing a cross-sectional view along line II-II of FIG. 1), selected to allow various components and devices and instruments and materials (such terms being used interchangeably herein without intent to limit), such as a guidewire (over which the catheter 110 and/or other devices may be advanced and guided), a cutting wire, other therapeutic devices/materials, etc., to pass through the catheter 110 to a treatment site. As may be further appreciated, the exterior of the catheter 110 has an outer diameter CD (as illustrated by FIG. 2, showing a cross-sectional view along line II-II of FIG. 1) selected to fit in the body passage in which the desired procedure is to be performed, or even within another tubular element (e.g., shaft, catheter, duodenoscope, endoscope, etc.) which is navigated within a body passage. Thus, the amount of space provided in the interior space 114s in the hollow wall 114 of the catheter 110 for placement of components is limited, Navigation-assisting equipment provided within the interior space 114s of the catheter 110 is appropriately sized (both lengthwise as well as in cross-section) and shaped to fit within the interior space 114s and to be appropriately arranged to detect contact of the distal end 113 of the catheter 110 with body tissue or a lumen wall, or to detect other application of force on the distal end 113 of the catheter 110.

An example of navigation-assisting equipment utilizing a sensor 120 positioned within the wall 114 of a catheter, such as within the interior space 114s in a wall 114 of a catheter 110, is illustrated schematically in FIG. 3. The sensor 120 may be any of a variety of pressure sensors capable of detecting pressure applied thereto or contact therewith or impact thereof against another object (such terms being used interchangeably herein with one another and other similar terms without intent to limit), including, without limitation, optical (e.g., fiberoptic), inductive, coil, piezoelectric, etc. sensors, as described in further detail below. The sensor 120 may include one or more pressure-sensitive elements 122 (illustrated schematically in FIG. 3) positioned relative to the distal end 113 of the catheter 110 to generate a signal based on relative movement or deformation of the sensor 120, such as caused by movement or deformation of the distal end 113 of the catheter 110. In some embodiments, the sensor 120 is a highly sensitive sensor, such as responding to increases in forces on the delivery catheter 110 ranging from 1-10 times, such as increases in forces ranging from 1-5 times, and/or responding to forces of approximately 1 g-100 g, such as forces of approximately 1-50 g, so that impact on the distal end 113 of the catheter 110 is detected to avert further impact (which may cause damage to or even puncture of the body tissue or lumen wall). It will be appreciated that other types of sensors, such as proximity, light, temperature, etc. may be used instead of or in addition to pressure sensors.

In some embodiments, described in further detail below, the distal end 113 of the catheter 110 is flexible so that if the distal end 113 impacts another object or obstacle (e.g., tissue wall or a lumen wall), the distal end 113 moves or deflects, and such movement or deflection actuates the sensor 120 to generate a signal indicating detection of pressure on the distal end 113 of the catheter 110, such as caused by impact or contact or encountering (such terms being used interchangeably herein with one another and other similar terms without intent to limit) of the distal end 113 of the catheter 110 with another object such as body tissue (e.g., papilla) or a lumen wall. The catheter sections or segments which move relative to each other may be referenced as a proximal pressure sensing segment 118 and a distal pressure sensing segment 116. It will be appreciated that although segments 116, 118 are referenced as "pressure sensing" such segments are not limited to sensing changes in pressure. In some embodiments, the proximal pressure sensing segment 118 is simply a distal portion of the catheter 110 and the distal pressure sensing segment 116 is a cap element at the distal-most free end of the catheter 110 to provide an atraumatic or blunt end or tip to the catheter 110. Inherent flexibility and/or resiliency of the wall 114 of the catheter 110 may cause actuation of the sensor 120, such as upon impact of the distal end 113 of the catheter 110 with another object (e.g., body tissue, a lumen wall, etc.) which causes deformation of the catheter 110 to be transmitted to the pressure-sensitive elements 122 of the sensor 120 to cause the pressure-sensitive elements 122 to generate a signal indicating the distal end 113 of the catheter 110 was impacted or otherwise contacted (such terms being used interchangeably herein with one another and other similar terms without intent to limit). A biasing element 130, such as a coil spring extending around the periphery of the catheter 110, or other biasing element known or heretofore known in the art, may be provided to impart flexibility and/or resiliency to the distal end 113 of the catheter 110 to function to actuate the pressure sensor 120.

In some embodiments, the proximal pressure sensing segment 118 and the distal pressure sensing segment 116 are separate elements separated by a gap 117 and movable relative to each other to actuate the pressure sensor 120. The interior wall 114i may extend across the gap 117 and at least partially into the proximal pressure sensing segment 118. The biasing element 130 may be provided in the gap 117 to provide resiliency to the distal end 113 of the catheter 110 and/or to maintain space between the distal pressure sensing segment 116 and the proximal pressure sensing segment 118 when in a rest or neutral position in which no pressure is exerted on the distal end 113 of the catheter 110. In the example of a distal end 113 of a catheter 110 illustrated in FIG. 3, the distal pressure sensing segment 116 may be a separate element movably mounted with respect to (e.g., axially) and distal to the proximal pressure sensing segment 118. For example, the distal pressure sensing segment 116 may be in the form of a movable ring element or pressure head separately formed from the distal end of the main catheter body forming the proximal pressure sensing segment 118. The distal pressure sensing segment 116 may be held in place relative to the proximal pressure sensing segment 118 so as not to separate therefrom, such as by being coupled to the biasing element 130 (which, in turn, would be coupled to the proximal pressure sensing segment 118 or another component of the catheter 110 or the delivery system). The exterior wall 114e (e.g., catheter jacket) of the catheter 110 may be configured to hold the distal pressure sensing segment 116 and the proximal pressure sensing segment 118 in place as well. Alternatively, or additionally, the distal pressure sensing segment 116 may be otherwise coupled to the body of the catheter 110.

In accordance with one aspect of the present disclosure, a sensor, such as a pressure sensor, is provided along the periphery or perimeter or circumference (such terms being used interchangeably herein without intent to limit) of the catheter 110, such as within the interior space 114s of the catheter 110, such as to provide enhanced directional information to assist in navigation of the catheter 110. In some embodiments, more than one sensor is provided along a periphery of the wall 114 of the catheter 110 to provide enhanced directional information to the medical professional indicative of the location of impact to the catheter wall 114. More particularly, signals from the various sensors of a plurality of sensors 120 may be mapped with respect to the periphery of the wall 114 of the catheter 110 such that a signal from a given sensor 120 is indicative of the location about the periphery of the wall 114 of the catheter 110 at which an obstacle was encountered and contacted. In some embodiments, at least three or four sensors 220 are provided about the periphery of the catheter 210. At least three sensors are provided to allow three-dimensional directionality (information in the X, Y, and Z axes). Four or more sensors 220 provide added directional information with respect to the X-Y plane such as by dividing the perimeter of the catheter 110 into quadrants which may be used to indicate more specifically the location of impact on the distal end 113 of the catheter 110. In some embodiments, the sensors 120 are spaced apart substantially equidistantly from one another. In some embodiments, the sensors 120 are correlated with a particular location about the periphery of the catheter 110 such that a signal generated by an individual one of the plurality of sensors 120 may be used to indicate a particular location about the perimeter or circumference of the catheter 110 which has contacted another element, such as a body lumen wall. More particularly, signals from the sensing elements may be processed comparatively to relay directional information to the medical professional so that the medical professional (or automated system) can determine the region of the distal end 113 of the catheter 110 which encountered another object (e.g., body tissue, a lumen wall, etc.) and thereby can determine the appropriate direction in which to navigate or maneuver the distal end 113 so as not to impact the object further, but, instead, to continue to be moved to reach the treatment site. The signal may be relayed to the medical professional navigating the catheter 110 so that the medical professional (or an automated system) can determine or decide the direction in which the catheter 110 should be maneuvered in order to pass the obstacle and reach the treatment site. Such information may also be associated or correlated with the steering components or equipment, the associated or correlated information being relayed to the medical professional to guide the medical professional in steering the catheter 110 in the appropriate direction to pass the obstacle and reach the treatment site.

In some embodiments, the forces sensed by the one or more sensors 120 are conveyed proximally (e.g., by appropriate wiring, or by wireless means) through the interior space 114s of the catheter 110 to an appropriate control unit, or the like, accessible to the medical professional controlling the catheter 110 and having a user interface (such as a display or interface with other components which generate information signals) to convey information useful for navigating the catheter 110. The control unit may be any control unit known or heretofore in the art to be capable of processing signals from pressure sensors as described herein and preferably also correlating such signals to locations about the perimeter of the catheter 110 and communicating such signals to the medical professional or other individual or navigational controller (e.g., computer system) navigating the catheter 110. Signals from each sensor 120 may be sent separately/individually to the control unit for processing. Information indicative of the particular sensor which generated a signal and the relative location or position of such sensor about the circumference of the catheter 110, thereby indicating the direction of impact of the catheter 110 with an obstacle such as a lumen wall or tissue wall, may be generated and provided to the medical professional. The control unit may correlate the location of the sensor(s) which generated the signal with the steering componentry so that the medical professional can use this information to determine the direction in which to steer the catheter 110 to continue to advance the catheter 110 without further obstruction to reach the treatment site. The control unit may include further navigational aids such as a six degree-of-freedom navigation sensor to track the catheter in three-dimensional space. Thus, the sensors are monitored, and, based on information from the sensors with regard to the location at which the distal end 113 of the catheter 110 encountered and contacted body tissue, a lumen wall, etc., the catheter 110 may be steered toward the target area or treatment site without damaging, penetrating, or otherwise further contacting, the body tissue, lumen wall, etc. Any of a variety of alerts, such as on-screen alerts, or more detailed information, may show which side(s) of the catheter 110 has been exposed to higher pressures.

As may be appreciated, additional componentry of navigation-assisting equipment, such as pressure transducers or pressure transmitters, wiring, mounting structures, etc., must be sized and shaped to fit within the interior space 114s within the catheter 110 and also to extend proximally through the catheterization system 100 to convey signals from the distal end 113 of the catheter 110 to the control unit to convey the desired information with regard to the distal end 113 of the catheter 110 to the medical professional. Depending on the specific construction of the navigation-assisting equipment (such as pressure-sensing components), the braiding process of the catheter 110 may provide stabilization structure for positioning and stabilizing the components in the interior space 114s in the wall 114 of the catheter 110. Alternatively, or in addition, a mount, such as a mounting ring, may be provided to stabilize components of the navigation-assisting equipment within the interior space 114s in the wall 114 of the catheter 110, and/or spaces may be filled, such as with adhesive and/or epoxy to hold components in place.

As discussed above, a sensor used in a navigation-assisting catheter in accordance with principles of the present disclosure may be any type of pressure sensor capable of sensing when the distal end 113 of the catheter 110 impacts or contacts another element, or other types of sensors providing information and/or feedback usable for navigational purposes. In some embodiments, the sensor 120 functions (e.g., generates a signal indicating application of pressure thereto) in response to relative movement of one or more elements. For instance, in the embodiments illustrated in FIGS. 4A, 4B, 5A, 5B, 6A, and 6B, a catheter 210 is provided with a sensor 220 in the form of one or more fiber optics 240 positioned within the wall 214 of the catheter 210. As illustrated in FIGS. 4A and 4B, the distal end 243 of the fiber optic 240 extends to a distal end of a proximal pressure sensing segment 218 of the catheter 210 at the distal end 213 of the catheter 210. The distal end 243 of the fiber optic 240 is at a proximal end of a gap 217 between the proximal pressure sensing segment 218 and a distal pressure sensing segment 216. A change in the gap between the distal end 243 of the fiber optic 240 and the proximal face 216p of the distal pressure sensing segment 216 (such as caused by the distal end 213 and the distal pressure sensing segment 216 of the catheter 110 encountering body tissue or a lumen wall) translates into a corresponding change in the interference pattern generated by reflection of light from the fiber optic 240 against the proximal face 216p of the distal pressure sensing segment 216. The pressure sensor 220 may determine pressure on the distal pressure sensing segment 216 such as by measuring a change in wavelength of reflected light off the proximal face 216p of the distal pressure sensing segment 216. A biasing element 230, such as a coil spring extending around the periphery of the catheter 210, may be provided between the distal pressure sensing segment 216 and the proximal pressure sensing segment 218 (such as within the interior space 214s of the catheter 210) to maintain space therebetween when in a rest or neutral position in which no pressure is exerted on the distal end 213 of the catheter 210 and/or to provide resiliency to the distal end 213 of the catheter 210. It will be appreciated that although segments 216, 218 are referenced as "pressure sensing" such segments are not limited to sensing changes in pressure.

To enhance navigation assisting capabilities of the sensor 220, a plurality of sensors 220 may be provided within the wall 214 the catheter 210, as illustrated in FIGS. 5A and 5B. As described above, provision of three or more sensor 220 permits signals from the sensors 220 to generate directional information useful to facilitate navigation of the catheter 110. Four or more sensors 220 may be provided in accordance with principles of the present disclosure to enhance directional sensitivity. The sensors 220 may be fiber optics 240 as in the embodiment of FIGS. 4A and 4B.

In some embodiments, such as illustrated in FIGS. 6A and 6B, a camera 250 may be provided as navigation-assisting equipment in addition to or instead of a sensor 220. In accordance with principles of the present disclosure, a camera 250 may be provided within the interior space 214s of the wall 214 of the catheter 210 instead of being passed through the working channel 212 of the catheter 210. As such, visualization for navigation purposes, as well as direct visualization once at the treatment site and performing the treatment, may be achieved with a camera without the camera occupying valuable space within the working channel 212 of the catheter 210 (allowing more room for working tools within the working channel 212). Moreover, positioning of the camera 250 within the wall 214 of the catheter 210 provides more reliable and stable positioning of the camera 250 during navigation through the body and as other working tools or other components are passed through the working channel 212 of the catheter 210, as the camera 250 is isolated or shielded or otherwise guarded from being moved or otherwise engaging or interacting with other working tools or other components, and may be stabilized against the catheter 210. It will be appreciated that although the embodiment illustrated in FIGS. 6A and 6B shows a camera 250 as well as sensors 220, provision of just a camera 250 without additional sensors may provide the desired navigational assistance in accordance with principles of the present disclosure. The sensors 220 may be fiber optics 240 as in the embodiment of FIGS. 4A and 4B.

As noted above, a sensor 120 used in a catheter 110, as generally illustrated in FIGS. 1A and 1B, in accordance with principles of the present disclosure may be any sensor, such as a pressure sensor, suitable for use in a small space as within the wall of a catheter 110 and for high sensitivity sensing capabilities as in navigating within the body. Another example of a sensor 120 which may be positioned within the wall 114 of a flexible and/or resilient distal end 113 of a catheter 110 is an inductive pressure sensor 320, as illustrated in FIGS. 7A and 7B. As with the embodiment of FIGS. 4A, 4B, 5A, 5B, 6A, and 6B, one or more inductive pressure sensors 320 may be distributed about the periphery of the wall 314 of the catheter 310 to facilitate force directionality determinations. The inductive pressure sensors 320 typically include a coil element 324 and an inductive rod element 326 positioned in the distal end 513 of the catheter 510 to detect pressure against the distal end 313 of the catheter 310. For instance, movement of the distal end 313 of the catheter 310, such as a result of the distal end 313 of the catheter 310 encountering and impacting another object, in the embodiment of FIGS. 7A and 7B causes relative movement of the distal pressure sensing segment 316 with respect to the proximal pressure sensing segment 318 (in this embodiment, against the biasing force of a biasing element 310), causing movement of the inductive rod element 326 relative to the coil element 324 to generate a signal. For instance, the inductive rod element 326 may extend distally from the coil element 324 and may move in response to or with movement of the distal pressure sensing segment 316 (such as upon contact with the proximal face 316p of the distal pressure sensing segment 316), and thereby move with respect to the coil element 324 to generate a signal indicative of force on the distal end 313 of the catheter 310.

Yet another type of sensor 120 which may be used in a catheter 110 in accordance with principles of the present disclosure is a piezoelectric sensor 420, as illustrated in the embodiments of FIGS. 8A and 8B. As known in the art, piezoelectric materials deform upon application of force thereto, generating an electrical signal indicative of such force. Impact to the distal end 413 of the catheter 410 transmits force to the piezoelectric sensor 420. In some embodiments, the impact may be a direct impact on the piezoelectric sensor 420 to cause deformation of the piezoelectric sensor 420 to generate a signal. In other embodiments, impact is as a result of relative movement of an optional separately movable distal pressure sensing segment 416 relative to the proximal pressure sensing segment 418 (e.g., via a biasing element 430 between the distal pressure sensing segment and the proximal pressure sensing segment 418, such as described above with reference to other embodiments disclosed herein) to generate a signal indicative of the distal end 413 of the catheter 410 impacting another object. As with the above-described embodiments of FIGS. 4A, 4B, 5A, 5B, 6A, 6B, 7A, and 7B, more than one piezoelectric sensor 420 may be provided about the perimeter of the wall 414 of the catheter 410 to facilitate determination of directionality of the force, and to use such information to facilitate navigation of the catheter 410. As may be appreciated, the piezoelectric sensors 420 may be actuated upon contact from different directions. As such, piezoelectric sensors 420 may provide directional pressure sensing capabilities to the catheter 410 of FIGS. 8A and 8B, not only based on the location of a given actuated piezoelectric sensor 420 relative to its location along the perimeter of the catheter 410, but also based on the direction of the force being applied to the given actuated piezoelectric sensor 420.

Instead of sensors 120 extending axially, such as to detect pressure on the distal end 113 of the catheter 110, a plurality of sensors 120 may extend radially across the distal end 513 of a catheter 510, such as shown in the embodiment illustrated in FIGS. 9A and 9B. Radially-extending sensors 520 may be placed at the distal end 513 of the catheter 510 in the distal pressure sensing segment 516 thereof, as illustrated, without force being transmitted to the sensors 520 via an intermediate element (e.g., a biasing element 130). However, it will be appreciated that a proximal pressure sensing segment 518 may be provided with the radially-extending sensors 520 mounted therein, and an intermediate element, such as a biasing element, being provided for force amplification purposes. When one of the sensors 520 contacts another object (e.g., upon moving the catheter 510 against an obstacle such as a tissue wall or lumen wall), the sensor 520 deforms or otherwise is actuated to generate a signal indicative of impact thereto. Radial orientation of the sensors 520 may afford a greater degree of sensitivity to directional information or location of impact to the distal end 513 of the catheter 510. Any sensor capable of fitting within the interior space 514*s* of the wall 514 of catheter 510 with sufficient sensitivity to forces (e.g., impact forces or bending forces) thereto may be used, such as piezoelectric sensors and/or strain gauges.

It is to be understood by one of ordinary skill in the art that the present discussion is a description of illustrative examples of embodiments only, and is not intended as limiting the broader aspects of the present disclosure. Although the foregoing disclosure describes a flexible, e.g., pressure-sensing, tip of a catheter, it will be appreciated that the principles described herein may be applied to other devices with a lumen therethrough. Embodiments of the present disclosure may be configured for use in conjunction with medical devices and systems (e.g., endoscopic accessory tools and/or guidewires inserted through a duodenoscope, etc.) for selective cannulation of the common bile duct (CBD) or pancreatic duct (PD) during an Endoscopic Retrograde Cholangio-Pancreatography (ERCP) procedure. However, it should be appreciated that embodiments of the present disclosure may also be used in a variety of other medical procedures which require navigating one or more accessory tools through ductal, luminal, or vascular anatomies, including, for example, interventional radiology procedures, balloon angioplasty procedures, thrombolysis procedures, angiography procedures, pulmonary procedures, and the like. The medical devices of the present disclosure are not limited to any particular type of endoscope, such as duodenoscopes, and may include a variety of medical devices for accessing body passageways, including, for example, catheters, duodenoscopes, ureteroscopes, bronchoscopes, colonoscopes, arthroscopes, cystoscopes, hysteroscopes, and the like. Further, the disclosed medical devices and systems may be inserted via different access points and approaches, e.g., percutaneously, endoscopically, laparoscopically, or some combination thereof.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A flexible elongate member defining a working channel sized and configured to allow instruments to be passed therethrough to perform a procedure with respect to a treatment site, said flexible elongate member comprising:
   an exterior tubular wall;
   an interior tubular wall positioned within the exterior tubular wall and defining an interior space between the exterior tubular wall and the interior tubular wall; and
   at least one sensor positioned within said interior space; wherein:
   at least one of said exterior wall and said interior wall defines a flexible and deflectable distal end of said flexible elongate member; and
   said at least one sensor is positioned in said flexible and deflectable distal end of said flexible elongate member and is configured to detect deflection of said flexible and deflectable distal end.

2. The flexible elongate member of claim 1, wherein said at least one sensor is a pressure sensor which detects impact of said distal end of said flexible elongate member against an object.

3. The flexible elongate member of claim 1, wherein said at least one sensor comprises one of an optic fiber, an inductive sensor, or a piezoelectric sensor.

4. The flexible elongate member of claim 3, wherein said distal end of said flexible elongate member comprises a proximal pressure sensing segment and a distal pressure sensing segment axially movable with respect to each other.

5. The flexible elongate member of claim 4, further comprising a biasing element biasing said proximal pressure sensing segment and said distal pressure sensing segment apart in a neutral configuration when said distal end of said flexible elongate member is not impacting an object.

6. The flexible elongate member of claim 4, wherein said at least one sensor is provided in said proximal pressure sensing segment, and movement of said distal pressure sensing segment relative to said proximal pressure sensing segment actuates said at least one sensor to generate a signal.

7. The flexible elongate member of claim 6, wherein said signal is indicative of said distal end of said flexible elongate member impacting an object.

8. The flexible elongate member of claim 7, wherein said at least one sensor comprises at least three pressure sensors spaced apart to indicate directionality of impact to said distal end of said flexible elongate member.

9. The flexible elongate member of claim 4, wherein:
   said at least one sensor is a fiber optic with a distal end at a distal end of said proximal pressure sensing segment spaced apart from a proximal face of said distal pressure sensing segment;
   and movement of said distal pressure sensing segment relative to said proximal pressure sensing segment causes a change in the interference pattern generated by reflection of light from said fiber optic against said proximal face of said distal pressure sensing segment indicative of pressure on said distal end of said flexible elongate member.

10. The flexible elongate member of claim 1, wherein said at least one sensor comprises at least three sensors providing directional information.

11. The flexible elongate member of claim 1, wherein said at least one sensor comprises at least four sensors equidistantly spaced about the periphery of said interior space.

12. The flexible elongate member of claim 1, further comprising a camera within said interior space.

13. A flexible elongate member comprising:
    a tubular wall comprising an exterior tubular wall and interior tubular wall positioned within the exterior tubular wall to define a working channel within said interior tubular wall sized and configured to allow instruments to be passed therethrough to perform a procedure with respect to a treatment site, and an interior space between said exterior tubular wall and said interior tubular wall and extending axially between a proximal end of said flexible elongate member and a distal end of said flexible elongate member; and
    at least one navigation-assisting sensor positioned within said interior space in a distal end of said flexible elongate member to generate a signal indicative of said distal end of said flexible elongate member encountering an object.

14. The flexible elongate member of claim 13, wherein said at least one navigation-assisting sensor is a pressure sensor capable of detecting impact of said distal end of said flexible elongate member against an object.

15. The flexible elongate member of claim 14, wherein said at least one pressure sensor comprises at least three pressure sensors providing directional information.

16. The flexible elongate member of claim 15, wherein said at least one pressure sensor comprises at least four pressure sensors equidistantly spaced about the periphery of said interior space.

17. The flexible elongate member of claim 13, wherein said at least one navigation-assisting sensor comprises one of an optic fiber, an inductive sensor, a piezoelectric sensor, or a camera.

18. A system comprising:
    a handle;
    a flexible elongate member extending axially between a proximal end coupled to said handle and a distal end, and comprising an exterior tubular wall and interior tubular wall positioned within the exterior tubular wall to define a working channel within said interior tubular wall sized and configured to allow instruments to be passed therethrough to perform a procedure with respect to a treatment site, and an interior space between said exterior tubular wall and said interior tubular wall; and at least one navigation-assisting sensor positioned within said interior space to generate a signal indicative of said distal end of said flexible elongate member encountering an object;

wherein:

at least one of said exterior wall and said interior wall defines a distal end of said flexible elongate member; and said at least one navigation-assisting sensor is positioned in said distal end of said flexible elongate member.

19. The system of claim 18, wherein said at least one navigation-assisting sensor comprises one of an optic fiber, an inductive sensor, a piezoelectric sensor, or a camera.

20. The system of claim 19, further comprising a control unit processing signals from said at least one navigation-assisting sensor to indicate directional information with regard to impact of said distal end of said flexible elongate member against an object.

\* \* \* \* \*